United States Patent [19]

Wasley

[11] 4,316,900
[45] Feb. 23, 1982

[54] PIPERAZINOPYRROLOBENZODIAZE-PINES

[75] Inventor: Jan W. F. Wasley, Chatham, N.J.

[73] Assignee: Ciba-Geigy Corporation, Ardsley, N.Y.

[21] Appl. No.: 68,827

[22] Filed: Aug. 22, 1979

Related U.S. Application Data

[63] Continuation-in-part of Ser. No. 933,358, Aug. 14, 1978, abandoned, which is a continuation-in-part of Ser. No. 839,696, Oct. 5, 1977, abandoned.

[51] Int. Cl.³ .................... A61K 31/55; C07D 487/18
[52] U.S. Cl. .................................. 424/250; 260/243.3; 424/274
[58] Field of Search ...................... 260/243.3; 424/250

[56] References Cited

PUBLICATIONS

Burger Medicinal Chemistry, 2nd Ed. Interscience, N.Y., N.Y., 1960, pp. 42 & 497.
Fuson, Adv. Org. Chem., p. 354, Wiley, N.Y., (1950).

Primary Examiner—Donald G. Daus
Assistant Examiner—D. B. Springer
Attorney, Agent, or Firm—Norbert Gruenfeld

[57] ABSTRACT 1,3,4,14b-Tetrahydro-2H,10H-pyrazino[1,2-a]pyrrolo[2,1-c][1,4]benzodiazepines, e.g. those of the formula

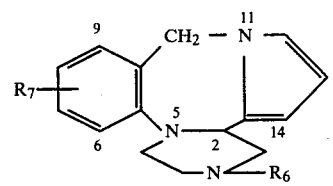

$R_6$=H, alkyl, alkenyl, alkynyl, (cycloalkyl or HO)-alkyl
$R_7$=H, halo or $CF_3$ acyl derivatives, N-oxides, quaternaries and acid addition salts thereof are antidepressants.

8 Claims, No Drawings

PIPERAZINOPYRROLOBENZODIAZEPINES

CROSS REFERENCE TO RELATED APPLICATIONS

This is a continuation-in-part of application Ser. No. 933,358, filed Aug. 14, 1978 (now abandoned), which in turn is a continuation-in-part of application Ser. No. 839,696, filed Oct. 5, 1977 (now abandoned).

SUMMARY OF THE INVENTION

The present invention concerns and has for its object the provision of new 1,3,4,14b-tetrahydro-2H,10H-pyrazino[1,2-a]pyrrolo[2,1-c][1,4]benzodiazepines, more particularly of those corresponding to Formula I

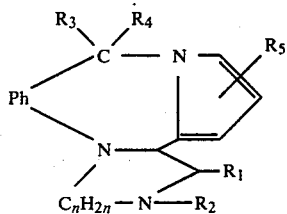

wherein each of $R_1$, $R_3$ and $R_4$ is hydrogen or lower alkyl; $R_2$ is hydrogen, lower or higher alkyl, lower alkenyl, lower alkynyl, 3 to 7 ring-membered cycloalkyl, cycloalkenyl or (cycloalkyl, hydroxy, amino, mono- or di-lower alkylamino, carboxy, lower carbalkoxy, carbamoyl, mono- or di-lower alkyl-carbamoyl, HPh, lower alkanoyl or HPhCO)-lower alkyl; Ph is 1,2-phenylene, unsubstituted or substituted by up to two members selected from lower alkyl, lower alkoxy, lower alkylthio, halogeno and trifluoromethyl; $C_nH_{2n}$ is lower alkylene separating both nitrogen atoms by 2 or 3 carbon atoms and $R_5$ is hydrogen, lower alkyl, carboxy, lower carbalkoxy or (hydroxy, amino, mono- or di-lower alkylamino)-lower alkyl; the lower alkoxycarbonyl, lower or higher alkanoyl, adamantoyl, carbamoyl, mono- or di-lower alkylcarbamoyl 3 to 7 ring membered cycloalkyl-carbonyl or HPhCO-derivatives; the 2-N-oxide, 2-lower alkyl or 2-HPh-lower alkyl quaternaries and salts thereof, derived from pharmaceutically acceptable acids or bases; as well as of corresponding pharmaceutical compositions and of methods for the preparation and application of said products, which are useful antidepressant agents suitable, for example, in the treatment or management of mental depression in mammals.

DESCRIPTION OF THE PREFERRED EMBODIMENTS

A lower alkyl group $R_1$, $R_2$, $R_3$, $R_4$, $R_5$ and/or such present in substituted 1,2-phenylene Ph, or phenyl HPh-group, is above all methyl, but also ethyl, n- or i-(propyl, butyl, pentyl, hexyl or heptyl), e.g. 2-methylpropyl or 3-methylbutyl. A higher alkyl group $R_2$ is, for example, n-(octyl, decyl, dodecyl, hexadecyl or octadecyl).

A lower alkenyl or lower alkynyl group $R_2$ is preferably such containing the multiple bond separated from the nitrogen atom by at least two carbon atoms, such as allyl, 2- or 3-butenyl or 3-methyl-2-butenyl; propargyl, 2- or 3-butynyl.

A 3 to 7 ring-membered cycloalkyl, cycloalkenyl or cycloalkyl-lower alkyl group $R_2$ is preferably cyclopropyl, cyclopentyl, cyclohexyl or cycloheptyl; 2- or 3-cyclopentenyl or -hexenyl; (cyclopropyl, cyclobutyl or cyclopentyl)-methyl or -ethyl.

A lower (hydroxy, amino, mono- or di-lower alkylamino, carboxy, carbalkoxy, carbamoyl, mono- or dialkylcarbamoyl or alkanoyl)-alkyl group $R_2$ is preferably such, wherein said heteroatoms (O or N) are separated from the ring-nitrogen atom by at least 2 carbon atoms, such as 2-(hydroxy, amino, methylamino, ethylamino, dimethylamino, diethylamino, carboxy, carbomethoxy, carbethoxy, carbamoyl, mono- or dimethylcarbamoyl, acetyl or propionyl)-ethyl or -propyl, 3-hydroxy-propyl or (carboxy, carbomethoxy, carbethoxy, carbamoyl, mono- or dimethylcarbamoyl or acetyl)-methyl.

A 1,2-phenylene radical Ph, or the (phenyl or benzoyl, i.e. HPh or HPhCO)-lower alkyl group $R_2$, is preferably unsubstituted or monosubstituted in the benzene ring by said substituents, for example methyl or ethyl; methoxy, ethoxy or i-propoxy; methylthio or ethylthio; fluoro, chloro, bromo or trifluoromethyl.

A lower alkylene group $C_nH_{2n}$ is especially ethylene, but also 1,2- or 1,3-propylene or 1,2-, 1,3- or 2,3-butylene.

A lower carbalkoxy or (hydroxy, amino, mono- or dialkylamino)-alkyl group $R_5$ is preferably carbomethoxy or carbethoxy or (hydroxy, amino, mono- or dimethylamino, mono- or diethylamino)methyl group.

Said acyl derivatives of the compounds of Formula I are preferably derived from those wherein $R_2$ is hydrogen, but also from those wherein $R_2$ and/or $R_5$ being (hydroxy, amino or lower-alkylamino)lower-alkyl, i.e. either amides or esters derived, for example, from said lower or higher aliphatic or cycloaliphatic acids, e.g. acetic, propionic, butyric, pivalic, decanoic, palmitic, hexahydrobenzoic or adamantylcarboxylic acid; carbamoic, mono- or dimethyl- or ethylcarbamoic or -carbonic acid; benzoic, toluic, anisic or halobenzoic acids.

Said N-oxides, lower alkyl or phenyl-lower alkyl quaternaries of the compounds of Formula I are derived from those wherein $R_2$ is different from hydrogen, and wherein only the 2-nitrogen atom is functionalized. The anions of said quaternaries and acid addition salts are preferably those of pharmaceutically acceptable acids, e.g. those listed below. Those compounds of Formula I, which contain carboxy within $R_2$ and/or $R_5$ also form salts with such bases, e.g. ammonia, mono-, di- or tri-lower alkylamines; lower alkyleneimines, morpholine, piperazine, pyridine or lower alkyl-derivatives of said cyclic bases; alkali metal or alkaline earth metal hydroxides.

The term "lower", referred to above or hereinafter in connection with organic radicals or compounds respectively defines such with up to 7, preferably up to 4, and advantageously those with one or two carbon atoms. The term "higher" defines analogous radicals with 8 to 20, preferably 8 to 16 carbon atoms.

The compounds of the invention exhibit valuable pharmacological properties, primarily antidepressant, activity. It is demonstrable in animal tests using advantageously mammals, e.g. mice, rats, guinea pigs or monkeys, as test objects. Said compounds can be applied to them enterally or parenterally, advantageously orally, or subcutaneously, intravenously or intraperitoneally, for example, within gelatin capsules or in the form of starchy suspensions or aqueous solutions respectively. The applied dosage may range between about 0.01 and 100 mg/kg/day, preferably between about 0.05 and 5 mg/kg/day, advantageously between about 0.1 and 0.5 mg/kg/day. Said antidepressant properties can be shown in mice by antagonism to clonidine analgesia. In this test system, the compounds of the invention are administered orally or intraperitoneally as aqueous solutions to groups of at least 10 male mice and 30 minutes thereafter 0.1 mg/kg of clonidine is intubated to them orally. 20 minutes later, they are injected with 3.75 mg/kg of phenyl-p-benzoquinone intraperitoneally and the number of mice that writhe is counted 5-15 minutes after injection. Any animal not writhing is considered a reactor and the $ED_{50}$ for the experimental drug and clonidine combination is determined by the Berkson Logit from the number of reactors.

Accordingly, the compounds of the invention are useful antidepressant agents, for example, in the treatment or management of mental depression. They are also useful intermediates in the preparation of other valuable products, especially of pharmacologically active compositions.

Particularly useful for said antidepressant utility are compounds of Formula I, in which each of $R_1$, $R_3$ and $R_4$ is hydrogen; $R_2$ is hydrogen, lower alkyl, lower alkenyl, lower alkynyl, 3 to 7 ring-membered cycloalkyl or (cycloalkyl, hydroxy or lower alkanoyl)-lower alkyl; Ph is 1,2-phenylene, (lower alkyl)-1,2-phenylene, (lower alkoxy)-1,2-phenylene, (lower alkylthio)-1,2-phenylene, (halogeno)-1,2-phenylene or (trifluoromethyl)-1,2-phenylene; n is the integer 2 or 3 and $R_5$ is hydrogen, lower alkyl or lower hydroxyalkyl; the lower alkanoyl, adamantoyl, carbamoyl, mono- or di-lower alkylcarbamoyl or HPhCO-derivatives, 2-N-oxides; 2-lower alkyl or 2-HPh-lower alkyl quaternaries; or pharmaceutically acceptable acid addition salts thereof.

Outstanding antidepressant compounds of the invention are those of Formula II

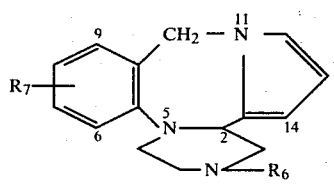

wherein $R_6$ is hydrogen, lower alkyl, lower alkenyl or (hydroxy or lower alkanoyl)-lower alkyl and $R_7$ is hydrogen, halogeno or trifluoromethyl; the lower alkanoyl derivatives, 2-N-oxides or pharmaceutically acceptable acid addition salts thereof.

Preferred and highly potent antidepressive compounds are those of Formula II, wherein $R_6$ is hydrogen, alkyl, alkenyl or hydroxyalkyl with up to 4 carbon atoms each or acetylethyl and $R_7$ is fluoro or chloro, preferably in the 7-position; the lower alkanoyl derivatives, 2-N-oxides or pharmaceutically acceptable acid addition salts thereof.

The compounds of the invention are prepared according to methods known per se, advantageously by reducing compounds of Formula III

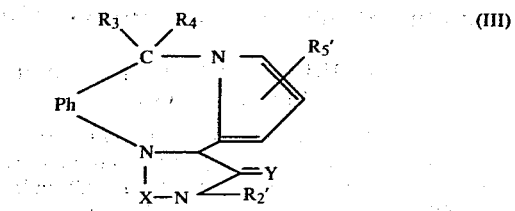

wherein $R'_2$ is hydrogen, lower alkyl, 3 to 7 ring-membered cycloalkyl or (cycloalkyl, hydroxy, amino, mono- or di-lower alkylamino or HPh)-lower alkyl; $R_3$ and $R_4$ are hydrogen or lower alkyl; $R'_5$ is hydrogen, lower alkyl, lower carbalkoxy or (hydroxy, amino, mono- or di-lower alkylamino)-lower alkyl; X is lower alkylene, mono- or dioxo-lower alkylene separating both nitrogen atoms by 2 or 3 carbon atoms and wherein oxo is attached to the carbon atoms adjacent to the nitrogen atoms, and Y is oxo, two hydrogens or hydrogen and lower alkyl; provided that at least one oxo group is present in X and if, desired, converting any resulting compound into another compound of Formula I.

The reduction of said lactams III is advantageously carried out with simple or complex light metal hydrides, such as boranes or alane; or preferably alkali metal aluminumhydrides or lower alkoxy-hydrides, e.g. lithium aluminumhydride, sodium tri-t-butoxy- or bis-(2-methoxy-ethoxy)-aluminumhydride.

The starting material can be prepared by reacting corresponding compounds of Formula III, wherein X represents two hydrogen atoms, with reactive derivatives of corresponding glycols, glycolic acids or dicarboxylic acids, such as lower alkyl esters, halides or anhydrides thereof, or reactive esters of said glycols or glycolic acid derivatives, for example with hydrohalic or aromatic sulfonic acids, 1,2-dibromethane or -propane, ethyl bromoacetate or -propionate, ethyl tosyloxy-acetate; diethyl oxalate or malonate, ethyl oxalyl chloride, oxylyl bischloride or malonic anhydride. Said precursors (III, X=H$_2$) can be prepared analogous to Il Farmaco, Ed. Sc. 24, Fasc. 3, page 276, or as illustrated by the examples herein.

The compounds of the invention so obtained can be converted into other compounds of Formula I according to known methods. Thus, for example, those with $R_2$ being hydrogen and/or $R_5$ being (amino or mono-lower alkylamino)-lower alkyl, or alkali metal, e.g. sodium salts thereof, can be reacted with reactive esters of unsubstituted or correspondingly substituted aliphatic or araliphatic alcohols such as methanol, ethanol, allyl alcohol, propargyl alcohol or benzyl alcohol respectively, e.g. such esterified by a strong inorganic or organic acid, above all a hydrohalic acid, e.g. hydrochloric, hydrobromic or hydriodic acid; sulfuric or an aromatic sulfonic acid, e.g. p-toluene or m-bromobenzene sulfonic acid, in order to obtain the corresponding N-substituted compounds or quaternaries respectively, depending on the molar amount of the alkylating agent employed. Conversely, resulting N-alkylated compounds can be converted into N-unsubstituted compounds, e.g. by catalytic hydrogenolysis of N-benzyl compounds, or reaction of N-lower alkyl derivatives with lower alkyl haloformates, e.g. ethyl chloroformate, to yield said N-acyl derivatives which, in turn, may be hydrolyzed to said unsubstituted compounds, preferably those with $R_2$=H, for example with aqueous bases, such as alkali metal hydroxides. Other acyl derivatives, eith amides or esters, can be obtained from compounds of Formula I with $R_2$ being hydrogen or $R_2$ and/or $R_5$ being (hydroxy, amino or monoalkylamino)-lower alkyl, and corresponding reactive acid derivatives, e.g. halides, simple or activated esters, such as alkyl or cyanoalkyl esters, anhydrides or cyanates. Resulting esters may be hydrolyzed as shown for said N-acyl derivatives, and unsaturated compounds, such as those with $R_2$ being lower alkenyl, alkynyl or cycloalkenyl, may be hydrogenated with catalytically activated hydrogen as shown above.

Resulting compounds of Formula I with $R_3$ and/or $R_4$ being hydrogen, can be converted to the corresponding lower alkyl derivatives by metallation with reactive organometallic agents, such as n-butyllithium or lithium diisopropylamide, followed by addition of said reactive esters of lower alkanols. Compounds I with $R_5$ being hydrogen, can also be converted to corresponding 12-acyl derivatives, e.g. by acylation with said derivatives of HO—X—OH (analogous to the preparation of III), or a trihaloacetyl halide, followed by treatment with an alkali metal lower alkoxide. Resulting 12-(carbalkoxy, carbalkoxycarbonyl or hydroxymethyl)-derivatives may be hydrolyzed as shown above and/or reduced to either 12-(methyl, hydroxymethyl or 2-hydroxyethyl)-compounds with said simple or complex light metal hydrides.

Resulting tertiary nitrogen compounds with $R_2$ different from hydrogen, can be converted into the N-oxides, for example with hydrogen peroxide or organic peracids, such as lower peralkanoic or perbenzoic acids, e.g. peracetic or m-chloroperbenzoic acid, advantageously at temperatures at or below room temperature with the latter, or up to 100° with diluted hydrogen peroxide in the presence of lower alkanoic acids, e.g. acetic acid. Care should be taken, especially with said peracids, in order to prevent overoxidation at overly long reaction times.

Finally, the compounds of the invention are either obtained in the free, basic form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide, basic salt or cation exchange, e.g. an alkali metal hydroxide or carbonate. Said acid addition salts are such of therapeutically acceptable inorganic or organic acids, such as strong metalloidic acids, for example hydrohalic, e.g. hydrochloric or hydrobromic acid; sulfuric, phosphoric, nitric or perchloric acid; but preferably such of aliphatic or aromatic carboxylic or sulfonic acids, e.g. formic, acetic, propionic, succinic, glycollic, lactic, malic, tartaric, citric, ascorbic, maleic, fumaric, hydroxymaleic, pyruvic, phenylacetic, benzoic, 4-aminobenzoic, anthranilic, 4-hydroxybenzoic, salicyclic, 4-aminosalicyclic, pamoic, nicothinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

In case mixtures of geometrical or optical isomers of the above compounds, e.g. I to III, are obtained, these can be separated into the single isomers by methods in themselves known, e.g. by fractional distillation, crystallization and/or chromatography. Racemic products can likewise be resolved into the antipodes, for example, by separation of diastereomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g. those of Formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

To the suspension of 12.8 g of 2-methyl-3,4-dioxo-1,3,4,14b-tetrahydro-10H-pyrazino[1,2-a]pyrrolo[2,1-c][1,4]benzodiazepine in 460 ml of tetrahydrofuran, 200 ml of 1-molar diborane in tetrahydrofuran are added while stirring and cooling with ice. The mixture is refluxed for one hour, again cooled and combined with 25 ml of acetic acid. It is evaporated, the residue taken up in 50 ml of 30% aqueous sodium hydroxide and the mixture extracted with methylene chloride. The extract is dried, evaporated, the residue dissolved in diethyl ether, the solution filtered and the filtrate evaporated, to yield the 2-methyl-1,3,4,14b-tetrahydro-10H—pyrazino[1,2-a]pyrrolo[2,1-c][1,4]benzodiazepine.

9.7 g thereof are dissolved in the minimum amount of isopropanol and the solution acidified with a concentrated solution of 4.45 g of maleic acid is isopropanol. The precipitate formed is collected and recrystallized from methanol-diethyl ether, to yield the corresponding mono-maleate melting at 176°–178°.

One may also reduce 2.35 g of said dioxo-starting material in 50 ml of methylene chloride with 20 ml of 1-molar alane in triethylamine, whereupon the mixture is evaporated. The residue is triturated with ethyl acetate-diethyl ether, chromatographed on 70 g of silica gel and eluted with methanol-chloroform (1:9). The eluate is evaporated and the residue salified as shown above, to yield a somewhat purer maleate melting at 180°–182°.

The starting material is prepared as follows: The mixture of 54.0 of N-potassium phthalimide, 50.0 g of o-nitrobenzyl chloride and 120 ml of dimethylformamide is refluxed for 3 hours and poured into 900 ml of ice-water while stirring. After 30 minutes, it is filtered, and the residue washed with water, to yield the N-o-nitrobenzyl-phthalimide melting at 190°–209°.

The mixture of 70.0 g thereof, 14.6 g of hydrazine hydrate and 600 ml of ethanol is refluxed for 4 hours and combined with 50 ml of concentrated hydrochloric acid. After 30 minutes, it is cooled to room temperature, filtered and the residue washed with water. The filtrate is concentrated, the aqueous concentrate filtered and the filtrate basified with 3 N aqueous sodium hydroxide. It is extracted with diethyl ether, the extract dried and evaporated, to yield the o-nitrobenzylamine.

To the solution of 7.6 g thereof in 25 ml of glacial acetic acid, 6.6 g of 2,5-dimethoxy-tetrahydrofuran are added and the mixture is refluxed for one hour. It is evaporated, the residue poured into ice water and the mixture extracted with ethyl acetate. The extract is washed with saturated aqueous sodium bicarbonate, dried and evaporated. The residue is taken up in diethyl ether, the solution decolorized with charcoal, filtered and evaporated, to yield the 1-(o-nitrobenzyl)-pyrrole.

Through the mixture of 13.42 g thereof, 140 ml of diethyl ether and 6.85 ml of chloroacetonitrile, hydrogen chloride is bubbled while stirring and cooling in an ice-salt bath. The saturated mixture is stirred at room temperature overnight, filtered and the residue suspended in 100 ml of water. It is extracted 3 times with 100 ml of ethyl acetate, warmed on the steam bath while stirring until all is dissolved, and the solution evaporated, to yield the 1-o-nitrobenzyl-2-chloroacetylpyrrole.

To the solution of 16.2 g thereof in 450 ml of ethanol, 14.10 g of N-methyl-benzylamine are added and the mixture is refluxed for 3 hours. It is evaporated, the residue taken up in methylene chloride, the solution washed with saturated aqueous sodium carbonate dried, filtered and evaporated. The residue is triturated with diethyl ether, to yield the 1-(o-nitrobenzyl)-2-(N-methyl-N-benzylaminoacetyl)-pyrrole.

The solution of 3.0 g thereof in 30 ml of glacial acetic acid is hydrogenated over 100 mg of platinum oxide at 2.7 atm and room temperature until the theoretical amount of hydrogen has been absorbed. It is filtered, the filtrate evaporated, the residue taken up in methylene chloride-diethyl ether and the solution washed with saturated aqueous sodium bicarbonate. It is dried, evaporated, the residue chromatographed on 30 g of silica gel and eluted with methanol-chloroform (1:9), to yield the 11-(N-methyl-N-benzylamino-methyl)-10,11-dihydro-5H-pyrrolo[2,1-c][1,4]benzodiazepine melting at 147°–149°.

The solution of 500 mg thereof in 35 ml of ethanol and 5 ml of glacial acetic acid is hydrogenated over 250 mg of 5% palladium on charcoal at 2.7 atm and 40° for 7 hours. The mixture is filtered, the filtrate evaporated and the residue taken up in methylene chloride. The solution is washed with saturated aqueous sodium carbonate, the aqueous phase extracted with methylene chloride and the combined organic solutions dried and evaporated, to yield the 11-(N-methylamino methyl)-10,11-dihydro-5H-pyrrolo[2,1-c][1,4]benzodiazepine.

The mixture of 300 mg thereof and 232 mg of diethyl oxalate is slowly heated to 140° during 45 minutes and to 180° during 15 minutes, at which temperature it is maintained for 30 minutes. It is cooled, diluted with benzene, chromatographed on silica gel and eluted with methanol-chloroform (1:9), to yield the 2-methyl-3,4-dioxo-1,3,4,14b-tetrahydro-10H-pyrazino [1,2-a]pyrrolo[2,1-c][1,4]benzodiazepine melting at 178°–179°.

EXAMPLE 2

To the suspension of 315 mg of 7-chloro-2-methyl-3,4-dioxo-1,3,4,14b-tetrahydro-10H—pyrazino[1,2-a]pyrrolo[2,1-c]-[1,4]-benzodiazepine in 20 ml of tetrahydrofuran, 6 ml of 1-molar diborane in tetrahydrofuran are added while stirring and cooling with ice. The mixture is refluxed for 2 hours, again cooled and combined with 1 ml of 6 N hydrochloric acid. It is evaporated, the residue taken up in 5 ml of 30% aqueous sodium hydroxide and the mixture extracted with methylene chloride. The extract is dried, evaporated, the residue dissolved in diethyl ether, and the solution combined with 97 mg of maleic acid in the minimum amount of acetone. The precipitate formed is collected to yield the 7-chloro-2-methyl-1,3,4,14b-tetrahydro-10H—pyrazino[1,2-a]pyrrolo[2,1-c][1,4]benzodiazepine mono-maleate melting at 200°–202°.

The starting material is prepared as follows: The mixture of 9.4 g of N-potassium phthalimide, 31.35 g of p-chloro-o-nitrobenzyl chloride and 75 ml of dimethylformamide is refluxed for 3 hours and poured into 180 ml of ice water while stirring. After 30 minutes, it is filtered and the residue washed with water to yield the N-p-chloro-o-nitrobenzyl-phthalimide melting at 190°–194°.

The mixture of 29.6 g thereof, 5.5 g of hydrazine hydrate and 300 ml of ethanol is refluxed for 4 hours and combined with 21 ml of concentrated hydrochloric acid. After 30 minutes, it is cooled to room temperature, filtered and the residue washed with water. The filtrate is concentrated, the aqueous concentrate filtered and the filtrate basified with 3 N aqueous sodium hydroxide.

It is extracted with diethyl ether, the extract dried and evaporated, to yield the p-chloro-o-nitrobenzylamine.

To the solution of 42.8 g thereof in 400 ml of glacial acetic acid 30.4 g of 2,5-dimethoxy-tetrahydrofuran are added and the mixture is refluxed for one hour. It is evaporated, the residue poured into ice water and the mixture extracted with ethyl acetate. The extract is washed with saturated aqueous sodium bicarbonate, dried and evaporated. The residue is taken up in diethyl ether, the solution decolorized with charcoal, filtered and evaporated, to yield the 1-(p-chloro-o-nitrobenzyl)-pyrrole.

Through the mixture of 4.26 g thereof, 20 ml of diethyl ether and 1.46 g of chloroacetonitrile, hydrogen chloride is bubbled while stirring and cooling in an ice-salt bath. The saturated mixture is stirred at room temperature overnight, filtered and the residue suspended in 50 ml of water. It is extracted 3 times with 50 ml of ethyl acetate. The extract is dried and evaporated, to yield the 1-(p-chloro-o-nitrobenzyl)-2-chloroacetyl-pyrrole.

To the suspension of 56.5 g thereof in 960 ml of ethanol, 21.8 of N-methyl-benzylamine and 18.2 g of triethylamine are added and the mixture is refluxed for 6 hours. It is evaporated, the residue taken up in chloroform, the solution washed with saturated aqueous sodium carbonate dried, filtered and evaporated. The residue is dissolved in diethyl ether, the solution filtered, the filtrate evaporated and the residue triturated with methanol, to yield the 1-(p-chloro-o-nitrobenzyl)-2-(N-methyl-N-benzylaminoacetyl)-pyrrole melting at 90°-93°.

To the solution of 1.0 g thereof in 30 ml of benzene 0.545 g of ethyl chloroformate are added and the mixture is refluxed for 4 hours. It is diluted with diethyl ether, washed with N hydrochloric acid and saturated aqueous sodium chloride, dried and evaporated, to yield the 1-(p-chloro-o-nitrobenzyl)-2-(N-methyl N-carbethoxyamino-acetyl)-pyrrole.

To the solution of 1.43 g thereof in 20 ml of tetrahydrofuran 15 ml of titanium trichloride are added dropwise and the mixture is stirred overnight at room temperature. It is made basic with 60 ml of 10% aqueous ammonia, filtered and the residue washed with methylene chloride. The organic phase is separated, washed with saturated aqueous sodium chloride, dried and evaporated, to yield the 8-chloro-11-(N-methyl-N-carbethoxyaminomethyl-5-H-pyrrolo[2,1-c][1,4]benzodiazepine.

To the solution of 430 mg thereof in 10 ml of ethanol, 760 mg of sodium borohydride are added and the mixture is stirred at room temperature overnight. It is acidified with 6 N hydrochloric acid, diluted with methylene chloride, washed with water and saturated aqueous sodium chloride, dried and evaporated. The residue is chromatographed on silica gel and eluted with ethyl acetate-methylene chloride (1:19), to yield the 8-chloro-11-(N-methyl-N-carbethoxyamino methyl)-10,11-dihydro-5H-pyrrolo [2,1-c][1,4]benzodiazepine.

The mixture of 200 mg thereof, 10 ml of ethanol and 3 ml of 20% aqueous sodium hydroxide is refluxed for 3 days and evaporated. The residue is taken up in water, the mixture extracted with methylene chloride, the extract dried and evaporated, to yield the 8-chloro-11-(N-methylamino methyl)-10,11-dihydro-5H-pyrrolo[2,1-c][1,4]benzodiazepine.

The mixture of 960 mg thereof, and 600 mg of diethyl oxalate is slowly heated to 140° during 45 minutes and to 180° during 15 minutes, at which temperature it is maintained for 30 minutes. It is cooled, evaporated, the residue washed with diethyl ether and triturated with ethyl acetate, to yield the 7-chloro-2-methyl-3,4-dioxo-1,3,4,14b-tetrahydro-10H—pyrazino[1,2-a]pyrrolo [2,1-c][1,4]-benzodiazepine melting at 203°.

EXAMPLE 3

To the solution of 1.9 g of 2-methyl-1,3,4,14b-tetrahydro-10H—pyrazino[1,2-a]pyrrolo[2,1-c][1,4]-benzodiazepine in 50 ml of benzene, 2.14 g of ethyl chloroformate are added and the mixture is refluxed for 3 days. It is diluted with diethyl ether, washed with N hydrochloric acid and with both saturated aqueous sodium chloride and sodium bicarbonate, dried and evaporated, to yield the 2-carbethoxy-1,3,4,14b-tetrahydro-10H—pyrazino[1,2-a]pyrrolo[2,1-c][1,4]-benzodiazepine showing in the NMR-spectrum peaks at 8.55(t), 6.60(m), 5.65(q) and 3.90(d) ppm, and in the mass-spectrum a molecular ion of 311.

EXAMPLE 4

The mixture of 930 mg of 2-carbethoxy-1,3,4,14b-tetrahydro-10H—pyrazino[1,2-a]pyrrolo[2,1-c][1,4]-benzodiazepine, 40 ml of ethanol and 20 ml of 20% aqueous potassium hydroxide is refluxed for 2 days. After cooling, it is diluted with ethyl acetate, washed with water, dried and evaporated. The residue is taken up in diethyl ether and the solution combined with 0.55 g of maleic acid in the minimum amount of acetone. The precipitate formed is collected and washed with diethyl ether, to yield the 1,3,4,14b-tetrahydro-2H,10H-pyrazino[1,2-a]pyrrolo[2,1-c][1,4]-benzodiazepine maleate melting at 173°-175°.

Analogously, the 7-chloro-1,3,4,14b-tetrahydro-2H,10H-pyrazino[1,2-a]pyrrolo[2,1-c][1,4]-benzodiazepine maleate is obtained (by hydrolysis with 20% aqueous sodium hydroxide) melting at 184°-186°.

EXAMPLE 5

To the solution of 4.8 g of 1,3,4,14b-tetrahydro-2H,10H-pyrazino[1,2-a]pyrrolo[2,1-c][1,4]-benzodiazepine in 20 ml of dimethyl formamide and 2.44 g of triethylamine, 2.91 g of allyl bromide are added dropwise while stirring. After one hour, the mixture is diluted with diethyl ether, washed with water and saturated aqueous sodium chloride and the aqueous phase is once more extracted with diethyl ether. The combined organic solutions are washed with saturated aqueous sodium bicarbonate, dried, evaporated and the residue triturated with diethyl ether, to yield the 2-allyl-1,3,4,14b-tetrahydro-10H—pyrazino[1,2-a]pyrrolo[2,1-c][1,4]-benzodiazepine melting at 130°-132°.

In the analogous manner, the (a) 2-(3-methyl-2-butenyl)-; (b) 2-propargyl-; (c) 2-cyclopropylmethyl-; (d) 2-carbomethoxymethyl and (e) 2-phenethyl-1,3,4,14b-tetrahydro-10H—pyrazino[1,2-a]pyrrolo[2,1-c][1,4]-benzodiazepines are prepared from equivalent amounts of the corresponding bromides. Said compounds of the invention (a) to (d) are converted into the acid addition salts listed below, as shown in Examples 1 and 2 herein, and crystallized from the various solvents as indicated. Said salts melt as follows: (a) maleate 152°-153° (isopropanol); (b) fumarate 138°-140° (ethanol); (c) maleate 189°-190° (isopropanol); (d) maleate 162°-164° (isopropanol-diethyl ether) and the free base (e) melts at 132°-134° (isopropanol).

EXAMPLE 6

The mixture of 1.5 g of 2-carbomethoxymethyl-1,3,4,14b-tetrahydro-10H—pyrazino[1,2-a]pyrrolo[2,1-c][1,4]-benzodiazepine and 10 ml of N aqueous sodium hydroxide is refluxed for 45 minutes until homogeneous. The solution is allowed to cool to room temperature and the precipitate formed is collected and washed with diethyl ether to yield the sodium salt of the 2-carboxymethyl 1,3,4,14b-tetrahydro-10H-pyrazino[1,2-a]pyrrolo[2,1-c][1,4]-benzodiazepine melting at 249°–250°.

EXAMPLE 7

Through the solution of 300 mg of 2-carbomethoxymethyl-1,3,4,14b-tetrahydro-10H-pyrazino[1,2-a]pyrrolo[2,1-c][1,4]-benzodiazepine in 5 ml of methanol, ammonia is bubbled for 2 hours while cooling to about −70°. The mixture is stirred overnight at room temperature, whereupon it is again saturated with ammonia and allowed to stand at room temperature for 2 days. It is evaporated and the residue triturated with diethyl ether, to yield the 2-carbamoylmethyl-1,3,4,14b-tetrahydro-10H-pyrazino[1,2-a]pyrrolo[2,1-c][1,4]-benzodiazepine melting at 198°–200°.

EXAMPLE 8

To the solution of 780 mg of 2-carbomethoxymethyl-1,3,4,14b-tetrahydro-10H-pyrazino[1,2-a]pyrrolo[2,1-c][1,4]-benzodiazepine in 20 ml of tetrahydrofuran, 150 mg of lithium aluminum hydride are added and the mixture is stirred for 2 days at room temperature. It is combined with 0.15 ml of water, 0.15 ml of 15% aqueous sodium hydroxide and 0.15 ml of water in this order filtered and the filtrate evaporated, to yield the 2-(2-hydroxyethyl)-1,3,4,14b-tetrahydro-10H-pyrazino[1,2-a]pyrrolo[2,1-c][1,4]benzodiazepine, which is converted into its mono-fumarate melting at 187°–189° with decomposition.

EXAMPLE 9

To the mixture of 100 mg of 1,3,4,14b-tetrahydro-2H,10H-pyrazino[1,2-a]pyrrolo[2,1-c][1,4]-benzodiazepine, 1 ml of N hydrochloric acid and 10 ml of water, the solution of 54.5 mg of sodium cyanate in 2 ml of water is added while stirring followed by 2 ml of tetrahydrofuran. After stirring overnight at room temperature, it is extracted with methylene chloride, the extract washed with saturated aqueous sodium carbonate, dried and evaporated, to yield the 2-carbamoyl-1,3,4,14b-tetrahydro-10H-pyrazino[1,2-a]pyrrolo[2,1-c][1,4]-benzodiazepine melting at 175°–177°.

EXAMPLE 10

The solution of 1.16 g of 2-allyl-1,3,4,14b-tetrahydro-10H-pyrazino[1,2-a]pyrrolo[2,1-c][1,4]-benzodiazepine in 25 ml of ethanol is hydrogenated over 40 mg of platinum oxide for 2.5 hours at room temperature and atmospheric pressure. It is filtered, the filtrate evaporated, the residue taken up in isopropanol and the solution acidified with maleic acid, to yield the 2-n-propyl-1,3,4,14b-tetrahydro-10H-pyrazino[1,2-a]pyrrolo[2,1-c][1,4]-benzodiazepine maleate melting at 157°–159°.

Analogously, the 2-(3-methyl-butyl)-1,3,4,14b-tetrahydro-10H-pyrazino[1,2-a]pyrrolo[2,1-c][1,4]-benzodiazepine maleate is prepared, melting at 146°–147°. Both of said compounds can also be obtained according to the method of Example 1.

EXAMPLE 11

To the solution of 500 mg of 1,3,4,14b-tetrahydro-2H,10H-pyrazino[1,2-a]pyrrolo[2,1-c][1,4]benzodiazepine in 7.5 ml of dimethylformamide and 350 mg of triethylamine, 470 mg of α-bromo-p-chloroacetophenone are added and the mixture is stirred at room temperature for 2 hours. It is diluted with 60 ml of diethyl ether, washed with water, dried and evaporated. The residue is taken up in 15 ml of chloroform and the solution again evaporated, to yield the 2-(p-chlorobenzoylmethyl)-1,3,4,14b-tetrahydro-10H-pyrazino[1,2-a]pyrrolo[2,1-c][1,4]benzodiazepine melting at 71°–74°.

EXAMPLE 12

According to the method illustrated by Examples 1 and 2, the 12-formyl-2-methyl-3,4-dioxo-1,3,4,14b-tetrahydro-10H-pyrazino[1,2-a]pyrrolo[2,1-c][1,4]benzodiazepine is reduced with diborane, to yield the 2,12-dimethyl-1,3,4,14b-tetrahydro-10H-pyrazino[1,2-a]pyrrolo[2,1-c][1,4]benzodiazepine, which is converted into its monomaleate melting at 173°–175°.

The starting material is prepared as follows:

The mixture of 170 mg of phosphorus oxychloride and 100 ml of dimethylformamide is stirred at room temperature for 30 minutes, whereupon the solution of 281 mg of 2-methyl-3,4-dioxo-1,3,4,14b-tetrahydro-10H-pyrazino[1,2-a]pyrrolo[2,1-c][1,4]benzodiazepine in 5 ml of methylene chloride is added dropwise. After 30 minutes, the mixture is refluxed for another 30 minutes and cooled to room temperature. It is combined with 1.5 g of sodium acetate in 5 ml of water, stirred for 30 minutes and the organic layer separated. It is washed with water, 5% aqueous sodium bicarbonate, dried, evaporated and the residue triturated with diethyl ether, to yield the 12-formyl-2-methyl-3,4-dioxo-1,3,4,14b-tetrahydro-10H-pyrazino[1,2-a]pyrrolo[2,1-c][1,4]benzodiazepine melting at 300°–302°.

EXAMPLE 13

The mixture of 500 mg of 2-methyl-1,3,4,14b-tetrahydro-10H-pyrazino[1,2-a]pyrrolo[2,1-c][1,4]benzodiazepine, 10 ml of methylene chloride and 0.5 ml of methyl iodide is stirred at room temperature for one hour. It is filtered and the residue washed with methylene chloride, to yield the 2,2-dimethyl-1,3,4,14b-tetrahydro-10H-pyrazino[1,2-a]pyrrolo[2,1-c][1,4]benzodiazepinium iodide melting at 258°–260° with decomposition.

EXAMPLE 14

To the solution of 5.1 g of 2-methyl-1,3,4,14b-tetrahydro-10H-pyrazino[1,2-a]pyrrolo[2,1-c][1,4]benzodiazepine in 100 ml of methylene chloride, 4.5 g of 85% m-chloroperbenzoic acid in 30 ml of methylene chloride are added and the mixture is stirred at room temperature for 5 hours. It is shaken with 100 ml of 10% aqueous sodium sulfite, stirred for one hour and the organic layer separated. It is washed with saturated aqueous sodium bicarbonate, dried and evaporated, to yield the 2-methyl-1,3,4,14b-tetrahydro-10H-pyrazino[1,2-a]pyrrolo[2,1-c][1,4]benzodiazepine-2-N-oxide melting at 143°–145°. It is dissolved in the minimum amount of methylene chloride, the solution chromatographed on neutral alumina and eluted with methylene chloride-methanol (49:1). The eluant is evaporated, the residue taken up in isopropanol and the solution acidified with maleic acid, to yield the corresponding monomaleate melting at 181°–183°.

EXAMPLE 15

To the solution of 140 mg of 2-methyl-1,4-dioxo-1,3,4,14b-tetrahydro-10H-pyrazino[1,2-a]pyrrolo[2,1-c][1,4]benzodiazepine in 5 ml of tetrahydrofuran, 2 ml of 1-molar diborane in tetrahydrofuran are added while stirring and cooling in ice. The mixture is allowed to stir at room temperature overnight and is then refluxed for 4 hours. After cooling to room temperature it is combined with 0.5 ml of glacial acetic acid, evaporated and the residue basified with 3 N aqueous sodium hydroxide. The mixture is extracted with methylene chloride, the extract dried, evaporated and the residue dissolved in diethyl ether. The solution is filtered and the filtrate evaporated to yield the 2-methyl-1,3,4,14b-tetrahydro-10H-pyrazino[1,2-a]pyrrolo[2,1-c][1,4]benzodiazepine, which is identical with that obtained according to Example 1; its monomaleate melts at 176°–178°.

The starting material is prepared as follows: To the stirred solution of 16 g of oxalyl chloride in 150 ml of diethyl ether, cooled to −50° by means of a solid carbon-dioxide-acetone bath, the solution of 7.36 g of pyrrole in 30 ml of diethyl ether is added at such a rate that the internal temperature of the mixture is maintained at −50°. The stirring is continued for 1 hour after completion of the addition and the mixture is poured slowly into the solution of 27.5 g of sarcosine ethyl ester in 150 ml of diethyl ether. The resulting precipitate is collected, extracted thoroughly with methylene chloride and the extract evaporated to yield the N-(2-pyrrylglyoxyl)-sarcosine ethyl ester melting at 114°.

To the solution of 5.5 g thereof in 30 ml of dimethyl formamide is added 1.07 g of a 50% sodium hydride suspension in mineral oil and 20 ml of dimethyl formamide. The mixture is heated to 60°–70° for 1 hour, cooled to room temperature and combined with the solution of 5 g of o-nitrobenzyl bromide in 20 ml of dimethyl formamide. The mixture is stirred at 45°–50° for 1 hour, cooled to room temperature, diluted with water and extracted with ethyl acetate. The extract is dried, evaporated and the residue triturated with diethyl ether to yield the N-(1-o-nitrobenzyl-2-pyrrylglyoxl)-sarcosine ethyl ester melting at 105°–108°.

The solution of 3.0 g thereof in 30 ml of ethyl acetate is hydrogenated over 100 mg of platinum oxide at 3 atm. until 3 mole equivalents of hydrogen are absorbed. The mixture is combined with 1.5 ml of glacial acetic acid and the uptake of hydrogen is finalized at 3 atm. and at 40°. It is filtered, the filtrate evaporated, the residue taken up in methylene chloride and purified by column chromatography on silica gel using 10% methanol-methylene chloride as eluant, to yield the N-10,11-dihydro-5H-pyrrolo[2,1-c][1,4]benzodiazepinylcarbonyl-sarcosine ethyl ester melting at 147°–148°.

To the suspension of 100 mg thereof in 10 ml of toluene is added 20 mg of sodium methoxide and the mixture refluxed for 1 hour. It is cooled, filtered and evaporated to yield 2-methyl-1,4-dioxo-1,3,4,14b-tetrahydro-10H-pyrazino[1,2-a]pyrrolo][2,1-c][1,4]benzodiazepine melting at 165°–167°.

EXAMPLE 16

To the hot solution of 10 g of 2-methyl-1,3,4,14b-tetrahydro-10H-pyrazino[1,2-a]pyrrolo[2,1-c][1,4]benzodiazepine (Example 1) in 300 ml of isopropanol is added the hot solution of 3.0 g of d-tartaric acid in 50 ml of isopropanol. The mixture is allowed to cool overnight to room temperature and the solids are collected by filtration. These are recrystallized from aqueous ethanol until the optical rotation of the liberated free base is constant (3 times), i.e., $[\alpha]_D 25 = +344.26°$ (c=1 in methanol). It is converted into the monomaleate melting at 190°–191° with decomposition.

Similar use of l-tartaric acid yields the corresponding antipode of the free base with $[\alpha]_D 25 = -358.89°$, the monomaleate of which melts at 188°–189° with decomposition.

EXAMPLE 17

To the solution of 800 mg of 2-methyl-5-oxo-1,3,4,5,15b-hexahydro-11H-[1,4]diazepino[1,2-a]pyrrolo[2,1-c][1,4]benzodiazepine in 50 ml of tetrahydrofuran, 6.2 ml of 1-molar diborane in tetrahydrofuran are added. The mixture is refluxed for 2 hours, cooled and stirred overnight at room temperature. It is combined with 2 ml of glacial acetic acid, evaporated and the residue basified with 3 N aqueous sodium hydroxide. The resulting mixture is extracted with methylene chloride, the extract dried, evaporated and the residue dissolved in the minimum amount of methylene chloride. The solution is chromatographed on silica gel and eluted with 10% methanol-methylene chloride to yield the 2-methyl-1,3,4,5,15b-hexahydro-11H[1,4]diazepino[1,2-a]pyrrolo[2,1-c][1,4]benzodiazepine of Formula I with $R_1=R_3=R_4=R_5=H$, $R_2=$methyl, Ph=1,2-phenylene and n=3. It is converted into the monofumarate melting at 174°–175°.

The starting material is prepared as follows: The solution of 1.5 g of 11-(N-methylaminomethyl)-10,11-dihydro-5H-pyrrolo[2,1-c][1,4]benzodiazepine (Example 1) in 7.5 ml of methyl acrylate is stirred at room temperature for 24 hours and the excess reagent is evaporated to yield the 11-(N-methyl-N-methoxycarbonylethylamino-methyl)-10,11-dihydro-5H-pyrrolo[2,1-c][1,4]benzodiazepine as an oil, which is chromatographed on silica gel and eluted with 2% methanol-methylene chloride.

The solution of 1.0 g thereof in 20 ml of tetrahydrofuran is added to the stirred solution of 475 mg of 2,2,6,6-tetramethylpiperidine (freshly distilled from calcium hydride) in 10 ml of tetrahydrofuran, followed by 1.37 ml of 2.45 molar n-butyl lithium in hexane at −75°. The mixture is stirred at this temperature for 30 minutes and then allowed to warm gradually to 0°. It is diluted with acetic acid-water (2:1), evaporated, the residue dissolved in methylene chloride, chromatographed on silica gel and eluted with 5% methanol-methylene chloride to yield the 2-methyl-5-oxo-1,3,4,5,15b-hexahydro-11H-[1,4]diazepino[1,2-a]pyrrolo-[2,1-c][1,4]benzodiazepine melting at 156°–158°.

EXAMPLE 18

To the solution of 2.5 g of 2-methyl-1,3,4,14b-tetrahydro-10H-pyrazino[1,2-a]pyrrolo[2,1-c][1,4]benzodiazepine (Example 1) in 25 ml of tetrahydrofuran is added 4.5 ml of 2.45 molar n-butyl lithium in hexane at room temperature while stirring under nitrogen. The pale yellow solution rapidly becomes cherry-red and the temperature rises about 7°. The mixture is stirred for an additional 45 minutes, whereupon it is treated with methyl iodide until the color of the solution is discharged. After stirring for a further 30 minutes the mixture is poured into 100 ml of water, and the product is extracted with diethyl ether. The extract is washed successively with water and brine, evaporated and the residual oil chromatographed on silica gel, using 2% methanol-methylene chloride as eluent, to yield the 2,10-dimethyl-1,3,4,14b-tetrahydro-10H-pyrazino[1,2,-a]pyrrolo[2,1-c][1,4]benzodiazepine which is converted to its mono maleate melting at 157°. The identical product is also obtainable according to the methods of Examples 1 and 15 by selecting o-nitro-α-methylbenzyl chloride or bromide respectively.

EXAMPLE 19

To the stirred solution of 1.3 g of 1,3,4,14b-tetrahydro-2H,10H-pyrazino[1,2-a]pyrrolo[2,1-c][1,4]benzodiazepine (Example 4) and 550 mg of triethylamine in 15 ml of tetrahydrofuran is added 765 mg of benzoyl chloride. After allowing the mixture to stir at room temperature overnight it is evaporated and the residue taken up in 100 ml of water. The mixture is extracted with diethyl ether, washed successively with water and brine, dried and evaporated, to yield 2-benzoyl-1,3,4,14b-tetrahydro-10H-pyrazino[1,2-a]pyrrolo[2,1-c][1,4]benzodiazepine melting at 137°-139° after recrystallization from isopropanol.

EXAMPLE 20

To the solution of 2.5 g of 2-(2-hydroxyethyl)-1,3,4,14b-tetrahydro-10H-pyrazino[1,2-a]pyrrolo[2,1-c]benzodiazepine (Example 8) and 935 mg of triethylamine in 72 ml of tetrahydrofuran is added 720 mg of acetyl chloride. The mixture is stirred at room temperature for 2 hours, evaporated and the residue extracted with methylene chloride. The extract is washed successively with water and brine, dried, filtered and evaporated to yield 2-(2-acetoxyethyl)-1,3,4,14b-tetrahydro-10H-pyrazino[1,2-a]pyrrolo[2,1-c][1,4]benzodiazepine, which is converted to its mono-fumarate melting at 156°-158° with decomposition.

Analogously, the free bases of the 2-[2-(n-hexanoyloxy, n-decanolyloxy, n-hexadecanoyloxy and 1-adamantylcarbonyloxy)-ethyl]-1,3,4,14b-tetrahydro-10H-pyrazino[1,2-a]pyrrolo[2,1-c][1,4]benzodiazepine are prepared, melting at 56°-58°, 59°-61°, 71°-73° and 47°-50° respectively.

EXAMPLE 21

348 g of 2-methyl-3,4-dioxo-1,3,4,14b-tetrahydro-10H-pyrazino[1,2-a]pyrrolo[2,1-c][1,4]benzodiazepine are added portionwise over 1 hour to 4,500 ml of tetrahydrofuran and 7,410 ml of 1-molar diborane in tetrahydrofuran while cooling with ice to 18° and stirring under nitrogen. The mixture is refluxed for 24 hours, again cooled to 5° and combined with 1,200 ml of glacial acetic acid followed by 900 ml of water. The solution is refluxed for 24 hours, evaporated and the residue taken up in 10,500 ml of methanol. The solution is again refluxed for 2 hours, evaporated, the residue dissolved in 3,000 ml of water and the pH of the solution adjusted to 14 with 1,200 ml of 10% aqueous sodium hydroxide. The mixture is extracted with diethyl ether, the extract dried, filtered and evaporated to yield the 2-methyl-1,3,4,14b-tetrahydro-10H-pyrazino[1,2-a]pyrrolo[2,1-c][1,4]benzodiazepine melting at 98°-100°.

307 g thereof are dissolved in 1,280 ml of absolute ethanol while refluxing, the solution is filtered, the filtrate cooled to 28° and combined with the 140.5 g of maleic acid in 294 ml of ethanol. The precipitate formed is collected, washed with cold ethanol and recrystallized from ethanol again to yield the corresponding mono-maleate melting at 183°-185°; it is somewhat purer than that obtained according to Example 1.

The starting material is prepared as follows: The mixture of 3,078 g of o-nitrobenzylamine and 2,670 g of 2,5-dimethoxytetrahydrofuran is added rapidly to 10,000 ml of glacial acetic acid at 86° while stirring under nitrogen. The mixture is stirred at 95° for 1.25 hours, cooled to 25° and combined with 30,000 ml of water. It is extracted with ethyl acetate, the extract is washed with 10% aqueous sodium hydroxide and 10% aqueous sodium chloride, filtered and evaporated to yield the 1-(o-nitrobenzyl)-pyrrole.

Through the mixture of 3,468 g thereof, 8,500 ml of tetrahydrofuran and 1,290 g of chloroacetonitrile, hydrogen chloride is bubbled for 3 hours while stirring and cooling to 5°-35°. The saturated suspension is stirred another hour at 17°, filtered, the residue suspended in 1,000 ml of tetrahydrofuran and filtered again, to yield the 1-o-nitrobenzyl-2-(1-imino-2-chloroethyl)-pyrrole hydrochloride, melting at 210°-212° with decomposition.

The suspension of 3,469 g thereof and 3,500 ml of water is stirred for one hour at 80°, thereafter cooled to 25° and filtered. The residue is washed with water, dried and 6,000 g thereof dissolved in 60,000 ml of ethanol while refluxing under nitrogen. The solution is filtered hot, concentrated by distilling 36,000 ml ethanol off, and allowed to cool to 25° overnight. The resulting suspension is filtered and the residue dried to yield the 1-o-nitrobenzyl-2-chloroacetylpyrrole melting at 112°-114°.

The suspension of 5,112 g thereof, 26,400 ml of toluene, 2,445 g of N-methylbenzylamine and 2,040 g of triethylamine is stirred under nitrogen at 93° for 6 hours and at room temperature overnight. It is combined with 20,000 ml of water, the aqueous phase separated, the organic phase washed with 10% aqueous sodium chloride and evaporated. The residue is dissolved in 20,000 ml of hot ethanol, the solution concentrated by distilling off 2,000 ml of ethanol, and allowed to stir overnight at room temperature. The crystals formed are filtered off, washed with ethanol and dried to yield the 1-(o-nitrobenzyl)-2-(N-methyl-N-benzylaminoacetyl)-pyrrole melting at 103°-105°.

The solution of 300 g thereof in 3,000 ml of ethyl acetate and 250 ml of glacial acetic acid is hydrogenated over 30 g of platinum oxide at atmospheric pressure and room temperature until the theoretical amount of hydrogen has been absorbed. It is filtered, the residue washed with ethyl acetate and the filtrate evaporated. The residue is taken up in methylene chloride, the solution washed with 2.5 N aqueous sodium hydroxide and saturated aqueous sodium chloride, dried and evaporated. The residue is triturated with diethyl ether to yield the 11-(N-methyl-N-benzylaminomethyl)-10,11-dihydro-5H-pyrrolo[2,1-c][1,4]benzodiazepine melting at 151°-152°.

To the solution of 142.5 g thereof in 2,000 ml of toluene and 45 g of triethylamine, 61 g of ethyl oxalyl chloride in 850 ml of toluene are added during 90 minutes while stirring at 10°-20°. After 4 hours the mixture is poured into 750 ml of water, the whole stirred for 20 minutes and the organic layer separated. It is washed with saturated aqueous sodium bicarbonate and sodium chloride each, dried, evaporated and the residue recrystallized from methanol, to yield the 10-ethyloxalyl-11-(N-methyl-N-benzylaminomethyl)-10,11-dihydro-5H-pyrrolo[2,1-c][1,4]benzodiazepine melting at 99°-101°.

(Utilization of greater amounts of ethyl oxalyl chloride result in the formation of the corresponding 3,10-bis-ethyloxalyl-compound melting at 115°–116°, which is less soluble in isopropanol than the former, and can be collected from concentrated solutions thereof by filtration.)

The solution of 6.9 g of said 10-ethyloxalyl-compound in 100 ml of ethanol and 27 ml of glacial acetic acid is hydrogenated over 1.65 g of 5% palladium on charcoal at 2.7 atm and 40° for about one hour. The mixture is filtered and the filtrate evaporated to yield the 2-methyl-3,4-dioxo-1,3,4,14b-tetrahydro-10H-pyrazino[1,2-a]pyrrolo[2,1-c]-[1,4]benzodiazepine melting at 178°–179°.

Hydrogenating said 3,10-bis-ethyloxalyl-compound analogously, the ethyl (2-methyl-3,4-dioxo-1,3,4,14b-tetrahydro-10H-pyrazino[1,2-a]pyrrolo[2,1-c][1,4]benzodiazepin-12-yl)-glycolate is obtained.

EXAMPLE 22

Reducing 200 mg of 12-formyl-2-methyl-3,4-dioxo-1,3,4-14b-tetrahydro-10H-pyrazino[1,2-a]pyrrolo[2,1-c][1,4]benzodiazepine with diborane according to Examples 1 or 2, the 2,12-dimethyl-1,3,4,14b-tetrahydro-10H-pyrazino[1,2-a]pyrrolo [2,1-c][1,4]benzodiazepine is obtained, which is converted to its monomaleate melting at 173°–175°.

Similarly, 200 mg of the ethyl (2-methyl-3,4-dioxo-1,3,4,14b-tetrahydro-10H-pyrazino[1,2-a]pyrrolo[1,4-]benzodiazepin-12-yl)-glycolate of Example 21 yield the 2-methyl-12-(2-hydroxyethyl)-1,3,4,14b-tetrahydro-10H-pyrazino[1,2-a]pyrrolo[2,1-c][1,4]benzodiazepine monomaleate melting at 153°–156°.

The starting material is prepared as follows: The mixture of 170 mg of phosphorus oxychloride and 100 ml of dimethylformamide is stirred at room temperature for 30 minutes, whereupon the solution of 281 mg of 2-methyl-3,4-dioxo-1,3,4-14b-tetrahydro-10H-pyrazino[1,2-a]pyrrolo[2,1-c][1,4]benzodiazepine in 5 ml of methylene chloride is added dropwise. After 30 minutes, the mixture is refluxed for another 30 minutes and cooled to room temperature. It is combined with 1.5 g of sodium acetate in 5 ml of water, stirred for 30 minutes and the organic layer separated. It is washed with water, 5% aqueous sodium bicarbonate, dried, evaporated and the residue triturated with diethyl ether, to yield the 12-formyl-2-methyl-3,4-dioxo-1,3,4,14b-tetrahydro-10H-pyrazino[1,2-a]pyrrolo[2,1-c][1,4]benzodiazepine melting at 300°–302°.

EXAMPLE 23

To the solution of 5.0 g of 2-methyl-1,3,4,14b-tetrahydro-10H-pyrazino[1,2-a]pyrrolo[2,1-c][1,4 benzodiazepine and 2.0 g of triethylamine in 50 ml of toluene is added 3.6 g of trichloroacetyl chloride. The mixture is stirred for 1 hour and then combined with 30 ml of water and 50 ml of methylene chloride. The organic phase is washed with water, dried and evaporated to yield the 2-methyl-12-trichloroacetyl-1,3,4-14b-tetrahydro-10H-pyrazino[1,2-a]pyrrolo[2,1-c][1,4]benzodiazepine.

5.4 g thereof are added to the solution of 100 mg of sodium in 75 ml of ethanol and the mixture is stirred at room temperature overnight. The precipitate formed is filtered off, washed with water and dried, to yield the 2-methyl-12-carbethoxy-1,3,4,14b-tetrahydro-10H-pyrazino[1,2-a]pyrrolo[2,1-c][1,4]benzodiazepine melting at 128°–130°, its monofumarate-monohydrate melts at 147°–150° with decomposition.

EXAMPLE 24

According to the methods illustrated by the previous examples (advantageously Examples 1 and 21), the following compounds of Formula II are obtained from equivalent amounts of the corresponding starting materials:

| No | $R_6$ | $R_7$ | Salt | m.p. °C. dec. |
|---|---|---|---|---|
| 1 | H | 9-$CH_3$ | maleate | 185–187 |
| 2 | $CH_3$ | 9-$CH_3$ | maleate | 172–174 |
| 3 | $CH_2=CH-CH_2$ | 9-$CH_3$ | maleate | 159–161 |
| 4 | H | 8-$CH_3$ | maleate | 169–171 |
| 5 | $CH_3$ | 8-$CH_3$ | maleate | 162–164 |
| 6 | $CH_3$ | 7-F | maleate | 179–181 |
| 7 | H | 7-$CF_3$ | maleate | 172–174 |
| 8 | $CH_3$ | 7-$CF_3$ | maleate | 189–191 |
| 9 | $(CH_2)_3-OH$ | H | fumarate | 201–203 |
| 10 | $(CH_2)_2-CO-CH_3$ | H | fumarate | 155–157 |
| 11 | $(CH_2)_{11}-CH_3$ | H | fumarate | 144–148 |

EXAMPLE 25

To the solution of 1.2 g of 1,3,4,14b-tetrahydro-2H,10H-pyrazino[1,2-a]pyrrolo[2,1-c][1,4]benzodiazepine in 20 ml anhydrous dimethylformamide is added 1 ml of triethylamine and 1.1 g of γ-chloro-p-fluorobutyrophenone. The mixture is stirred at room temperature for 24 hours, followed by refluxing for an additional 4 hours. It is allowed to cool to room temperature, poured into 200 ml of water and extracted with diethyl ether. The extract is dried, evaporated and the residue dissolved in the minimum amount of methylene chloride. The solution is chromatographed on silica gel using methylene chloride as eluant. The eluted solution is evaporated and the residue neutralized with maleic acid in isopropanol, to yield the 2-(3-p-fluorobenzoyl-propyl)-1,3,4,14b-tetrahydro-10H-pyrazino[1,2-a]pyrrolo[2,1-c][1,4]benzodiazepine monomaleate, melting at 128°–130°.

EXAMPLE 26

To a stirred solution of 3.1 g of 2-(3-oxo-n-butyl)-1,2,3,14b-tetrahydro-10H-pyrazino[1,2-a]pyrrolo[2,1-c][1,4]benzodiazepine (Example 24, No. 10) in 100 ml of diethyl ether is added 550 mg of lithium aluminumhydride in small portions. The mixture is stirred at room temperature overnight, combined with 0.6 ml of water, 0.6 ml of 15% aqueous sodium hydroxide and 0.6 ml of water in this order, filtered and evaporated. The residue is taken up in the minimum amount of isopropanol and the solution neutralized with fumaric acid, to yield the 2-(3-hydroxy-n-butyl)-1,3,4,14b-tetrahydro-10H-pyrazino[1,2-a]pyrrolo[2,1-c][1,4]benzodiazepine monofumarate melting at 181°–183°.

EXAMPLE 27

Preparation of 10,000 tablets each containing 5 mg of the active ingredient

| Formula: | |
|---|---|
| 2-methyl-1,3,4-14b-tetrahydro-10H-pyrazino[1,2-a]pyrrolo[2,1-c][1,4]benzodiazepine monomaleate | 50.00 g |
| Lactose | 1,157.00 g |
| Corn starch | 75.00 g |

-continued

| Formula: | |
|---|---|
| Polyethylene glycol 6,000 | 75.00 g |
| Talcum powder | 75.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 28

Preparation of 10,000 capsules each containing 10 mg of the active ingredient:

| Formula: | |
|---|---|
| 2-methyl-1,3,4-14b-tetrahydro-10H-pyrazino[1,2-a]pyrrolo[2,1-c]-[1,4]benzodiazepine monomaleate | 100.0 g |
| Lactose | 1,800.0 g |
| Talcum powder | 100.0 g |

Procedure:

All the powders are passed through a screen with openings of 0.6 mm. Then the drug substance is placed in a suitable mixer and mixed first with the talcum, then with the lactose until homogeneous. No. 3 capsules are filled with 200 mg, using a capsule filling machine.

Analogously tablets or capsules are prepared from the remaining compounds of the invention, e.g. those illustrated by the previous examples.

What is claimed is:

1. A 1,3,4,14b-tetrahydro-2H,10H-pyrazino[1,2-a]pyrrolo[2,1-c]benzo-diazepine compound of the formula

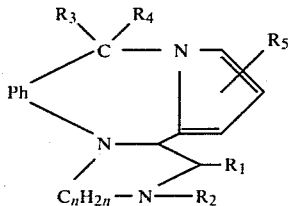

wherein each of $R_1$, $R_3$ and $R_4$ is hydrogen or methyl; $R_2$ is hydrogen, lower or higher alkyl, lower alkenyl, lower alkynyl, 3 to 7 ring-membered cycloalkyl, cycloalkenyl or cycloalkyl-lower alkyl, hydroxy-lower alkyl, amino-lower alkyl, mono- or di-lower alkylamino-lower alkyl, carboxy-lower alkyl, lower carbalkoxy-lower alkyl, carbamoyl-lower alkyl, mono- or di-lower alkylcarbamoyl-lower alkyl, phenyl -lower alkyl as defined by HPh-lower alkyl, lower alkanoyl-lower alkyl, or benzoyl-lower alkyl as defined by HPHCO- lower alkyl; Ph is 1,2-phenylene, unsubstituted or substituted by one member selected from lower alkyl, lower alkoxy, lower alkylthio, halogeno and trifluoromethyl; $C_nH_{2n}$ is lower alkylene separating both nitrogen atoms by 2 carbon atoms and $R_5$ is hydrogen, lower alkyl, carboxy, lower carbalkoxy, hydroxy-lower alkyl, amino-lower alkyl, mono- or di-lower alkylamino- lower alkyl; the lower alkoxy- carbonyl, lower or higher alkanoyl, adamantoyl, carbamoyl, mono- or di-lower alkylcarbamoyl, 3 to 7-ring membered cycloalkyl-carbonyl or HPhCO-derivatives or those compounds with $R_2$ and/or $R_5$ being (hydroxy, amino or lower alkylamino)-lower alkyl, or $R_2$ being hydrogen; the 2-N-oxide of those compounds with $R_2$ being different from hydrogen; and salts thereof, derived from pharmaceutically acceptable acids or ammonium or alkali metal bases.

2. A compound as claimed in claim 1, in which formula each of $R_1$, $R_3$ and $R_4$ is hydrogen; $R_2$ is hydrogen, lower alkyl, lower alkenyl, lower alkynyl, 3 to 7 ring-membered cycloalkyl, cycloalkyl-lower alkyl, hydroxy-lower alkyl or lower alkanoyl -lower alkyl; Ph is 1,2-phenylene, (lower alkyl)-1,2-phenylene, (halogeno)-1,2-phenylene or (trifluoromethyl)-1,2-phenylene; n is the integer 2 and $R_5$ is hydrogen, lower alkyl or lower hydroxyalkyl; the lower alkanoyl, adamantoyl, carbamoyl, mono- or di-lower alkylcarbamoyl or HPhCO-derivatives of these compounds with $R_2$ and/or $R_5$ being lower hydroxyalkyl or $R_2$ being hydrogen; the 2-N-oxide of those compounds with $R_2$ being different from hydrogen; or pharmaceutically acceptable acid addition salts thereof.

3. A compound as claimed in claim 1 and corresponding to the formula

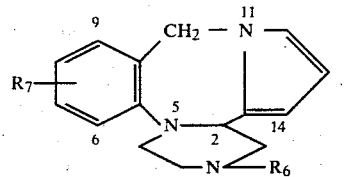

wherein $R_6$ is hydrogen, lower alkyl, lower alkenyl or (hydroxy or lower alkanoyl)- lower alkyl and $R_7$ is hydrogen, halogeno or trifluoromethyl; the lower alkanoyl derivatives of those compounds with $R_6$ being lower hydroxyalkyl or hydrogen; the 2-N-oxides of those compounds with $R_6$ being different from hydrogen; or pharmaceutically acceptable acid addition salts thereof.

4. A compound as claimed in claim 3, in which formula $R_6$ is hydrogen, alkyl, alkenyl or hydroxyalkyl with up to 4 carbon atoms each or acetylethyl and $R_7$ is fluoro or chloro; the lower alkanoyl derivatives of those compounds with $R_6$ being hydroxyalkyl or hydrogen; the 2-N-oxides of those compounds with $R_6$ being different from hydrogen; or pharmaceutically acceptable acid addition salts thereof.

5. A compound as claimed in claim 4, wherein the substituent $R_7$ is the 7-position.

6. A compound as claimed in claim 3 and being the 2-methyl-1,3,4,14b-tetrahydro-10H-pyrazino[1,2-a]pyrrolo[2,1-c][1,4]benzodiazepine, or pharmaceutically acceptable acid addition salts thereof.

7. An antidepressant pharmaceutical composition comprising an antidepressively effective amount of a compound as claimed in claim 1, together with a pharmaceutical excipient.

8. A method of treating depression in mammals, which comprises administering to them enterally or parenterally an effective amount of a composition as claimed in claim 7.

* * * * *

UNITED STATES PATENT AND TRADEMARK OFFICE
CERTIFICATE OF CORRECTION

PATENT NO. : 4,316,900
DATED : FEBRUARY 23, 1982
INVENTOR(S) : JAN W.F. WASLEY

It is certified that error appears in the above—identified patent and that said Letters Patent is hereby corrected as shown below:

Claim 1, Column 19, Line 65 reads:

HPHCO- lower alkyl; Ph is 1,2-phenylene, unsubsti-

Should read:

-- HPhCO- lower alkyl; Ph is 1,2-phenylene, unsubsti- --

Signed and Sealed this

Twenty-ninth Day of June 1982

[SEAL]

Attest:

Attesting Officer

GERALD J. MOSSINGHOFF

Commissioner of Patents and Trademarks